United States Patent [19]

Tzikas

[11] 4,351,975
[45] Sep. 28, 1982

[54] PROCESS FOR PREPARING CHLORINATED COMPOUNDS

[75] Inventor: Athanassios Tzikas, Pratteln, Switzerland

[73] Assignee: Ciba-Geigy AG, Basel, Switzerland

[21] Appl. No.: 247,087

[22] Filed: Mar. 24, 1981

[30] Foreign Application Priority Data

Mar. 25, 1980 [CH] Switzerland ................. 2324/80

[51] Int. Cl.$^3$ ............................................. C07C 17/12
[52] U.S. Cl. ................................. 570/209; 570/208; 570/144
[58] Field of Search ............. 570/209, 208, 147, 144, 570/127

[56] References Cited

U.S. PATENT DOCUMENTS 4,190,609  2/1980  Len .................................. 570/209

*Primary Examiner*—Delbert E. Gantz
*Assistant Examiner*—Joseph A. Boska
*Attorney, Agent, or Firm*—Wenderoth, Lind & Ponack

[57] ABSTRACT

A process for the preparation of monochlorinated and dichlorinated bis-(perhalomethyl)-benzenes of the formula (I) by reacting bis-(perhalomethyl)-benzenes of the formula (II) with elementary chlorine in chlorosulfonic acid as the reaction medium, at a temperature of, preferably, 0° to 10° C. The present invention makes it possible to obtain pure compounds of the formula (I), in high yields, in a single process step.

8 Claims, No Drawings

PROCESS FOR PREPARING CHLORINATED COMPOUNDS

The invention relates to a process for preparing compounds of the general formula

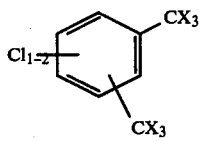

in which the X's are each halogen and may be identical or different, wherein a compound of the general formula

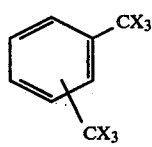

is reacted with elementary chlorine in chlorosulfonic acid at temperatures of $-10°$ to $+25°0$ C.

It is known from the literature that compounds of the formula (I) may be prepared by reacting compounds of the formula (II) with elementary chlorine at temperatures of 114° to 185° C. (cf. U.S. Pat. No. 2,394,422; U.S. Pat. No. 2,601,310; J. Org. Chem. 1976, 3 580; J. Amer. Chem. Soc. 69, 947), mixtures of monochlorinated and dichlorinated compounds and/or isomer mixtures being isolated, so that troublesome separation operations become necessary. Reactions of compounds of the formula (II) in sulfuryl chloride and disulfur dichloride (cf. Macromolecules 1974, 732) have the disadvantage of an unfavourable consumption of reagents and of requiring troublesome purification steps. In preparing the compounds mentioned on a large industrial scale, reactions at high temperatures, and additional purification steps entailing low yields, are expensive and therefore undesirable.

It is therefore the object of the present invention to prepare pure compounds of the formula (I) in high yields in a single process step, with elimination of the disadvantages recited above.

This object is achieved, according to the present invention, by reacting compounds of the formula (II) in accordance with the process mentioned at the outset. Surprisingly, pure compounds of the formula (I) are obtained in high yields under these conditions. Accordingly, the process according to the invention permits the preparation of compounds of the formula (I) in a simple and economical manner.

In the compounds of the formula (I), the $CX_3$ groups may be in the o-, m- or p-position relative to one another. The halogens within each $CX_3$ group may be identical or different.

The starting compounds employed for the process according to the invention are xylenes of the formula (II), whose methyl groups are halogenated, preferably compounds wherein the X's may be identical or different and are fluorine, chlorine or bromine.

The starting compounds of the formula (II) are known or can be prepared by known methods. Examples are 1,2-bis-(trifluoromethyl)-benzene, 1,3-bis-(trifluoromethyl)-benzene, 1-trichloromethyl-3-trifluoromethylbenzene, 1-tribromomethyl-3-trifluoromethylbenzene, 1-chlorodifluoromethyl-3-trifluoromethylbenzene, 1,3-bis-(dichlorofluoromethyl)-benzene, 1,3-bis-(trichloromethyl)-benzene, 1-tribromomethyl-3-trichloromethylbenzene, 1,3-bis-(tribromomethyl)-benzene, 1,4-bis-(trifluoromethyl)-benzene, 1-trichloromethyl-4-trifluoromethylbenzene, 1-tribromomethyl-4-trifluoromethylbenzene, 1-dichlorofluoro-methyl-4-chlorodifluoromethylbenzene, 1,4-bis-(trichloromethyl)-benzene, 1-tribromomethyl-4-trichloromethylbenzene and 1,4-bis-(tribromomethyl)-benzene.

In particular, 1,3- or 1,4-bis-(perhalomethyl)-benzenes, preferably 1,3- or 1,4-bis-(perchloromethyl)-benzene and 1,3-bis-(perfluoromethyl)-benzene, are employed as starting materials.

The particularly valuable compound of the formula

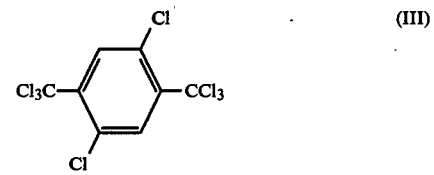

is prepared by reacting 1,4-bis-(trichloromethyl)-benzene with chlorine to give the compound of the formula (III).

The reaction according to the invention is carried out in chlorosulfonic acid as the reaction medium, at temperatures of, preferably, 0° to 10° C. The reaction with elementary chlorine is carried out under atmospheric pressure, in particular using a catalytic amount of iodine.

The reaction as a rule requires 3 to 5 hours, depending on the rate of introduction of chlorine gas.

The process for the preparation of monochlorinated or dichlorinated products is influenced by the halogen substituents of the $CX_3$ groups and by the position of the latter in the benzene nucleus; the process can be controlled through the amounts of chlorine employed and through the reaction temperature.

To work up the products of the process, the suspension is poured out onto ice, the mixture is filtered, and the filter residue is washed with cold water until neutral, and is dried. Pure products are obtained in high yield.

The compounds obtained by the process according to the invention are valuable intermediates for the preparation of dyes, pharmaceuticals, polymeric products and pigmentary products. For example, condensation of the products with 1,2-diaminoanthraquinones give valuable vat dyes.

In the examples which follow, parts and percentages are by weight, unless stated otherwise, and temperatures are in degrees centrigrade. Parts by weight bear the same relation to parts by volume as that of the gram to the cubic centimeter.

EXAMPLE 1

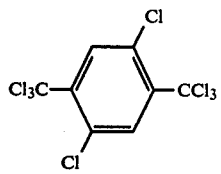

240 parts of chlorosulfonic acid are introduced, at room temperature, into a reaction vessel, and 62.6 parts of 1,4-bis-(trichloromethyl)-benzene and 2 parts of iodine are added. The suspension is cooled to 5° and 30 parts of chlorine are introduced in the course of 4 hours at 5°–10°. The suspension is then poured out onto ice and filtered cold. The filter residue is washed neutral with ice-cold water. It is then dried in a vacuum drying cabinet at 60°. 73.7 parts (96% of theory) of pure 2,5-dichloro-1,4-bis-(trichloromethyl)-benzene, of melting point 202°–203°, are obtained.

Analysis for chlorine - calculated: 74.3%, found: 74.05%.

Example 2

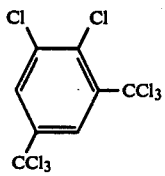

240 parts of chlorosulfonic acid are introduced, at room temperature, into a reaction vessel, and 62.6 parts of 1,3-bis-(trichloromethyl)-benzene and 2 parts of iodine are added. The suspension is cooled to 0° and 30 parts of chlorine are introduced in the course of about 4 hours at 0° to 5°. The suspension is then poured out onto ice and filtered cold. The filter residue is washed neutral with ice-cold water. It is then dried in a desiccator. 72 parts of 4,5-dichloro-1,3-bis-(trichloromethyl)-benzene are obtained; melting point, after recrystallisation from ethanol, 61°–62°.

Analysis for chlorine - calculated: 74.3%, found: 74.35%.

The structure was established by analysis of the $^{13}$C-NMR data.

EXAMPLE 3

130 parts of chlorosulfonic acid are introduced, at room temperature, into a reaction vessel, and 42.8 parts of 1,3-bis-(trifluoromethyl)-benzene and 2 parts of iodine are added. The suspension is cooled to 0° and 30 parts of chlorine are introduced in the course of 5 hours at 0° to 5°. The suspension is then poured out onto ice and the organic phase is separated from the aqueous phase. The organic phase is washed neutral with ice-cold water and is dried over calcined sodium sulfate. 38 parts of 5-chloro-1,3-bis-(trifluoromethyl)-benzene, of boiling point 111° to 112°, are obtained.

Analysis for chlorine - calculated: 14.28%, found: 14.02%.

Analysis for fluorine - calculated: 45.8%, found: 45.4%.

The structure was established by analysis of the $^{13}$C-NMR data.

EXAMPLE 4

19 parts of 2,5-dichloro-1,4-bis-(trichloromethyl)-benzene and 23.8 parts of 1,2-diaminoanthraquinone in 200 parts by volume of 98% or 100% strength sulfuric acid are stirred for 4 hours at 130°. When the suspension has cooled, it is poured out onto ice/water and filtered, and the filter residue is washed neutral and then treated with potassium hypochlorite solution. The resulting dye, of the formula

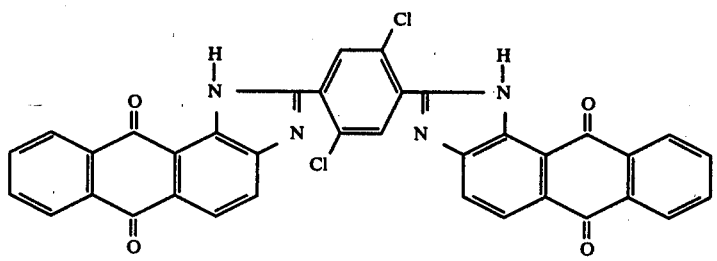

dyes cotton, by the vat-dyeing method, in greenish yellow shades having good fastness characteristics.

What is claimed is:

1. A process for the preparation of a compound of the general formula

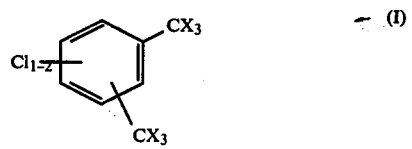

in which the X's are each halogen and may be identical or different, wherein a compound of the general formula

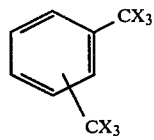

is reacted with elementary chlorine in chlorosulfonic acid at temperatures of −10° to +25° C.

2. A process according to claim 1, wherein a compound of the formula (II), in which the X's, which may be identical or different, are fluorine, chlorine or bromine, is used as the starting material.

3. A process according to either of claims 1 or 2, wherein the starting compound of the formula (II) is reacted with elementary chlorine at temperatures of 0° to 10° C.

4. A process according to any one of claims 1 to 3, wherein the chlorination is carried out in the presence of a catalytic amount of iodine.

5. A process according to any one of claims 1 to 4, wherein a 1,3- or 1,4-bis-(perhalomethyl)-benzene is used as the starting compound.

6. A process according to any one of claims 1, 3 and 4, wherein 1,3- or 1,4-bis-(perchloromethyl)-benzene is used as the starting compound.

7. A process according to any one of claims 1, 3 4, wherein 1,3-bis-(perfluoromethyl)-benzene is used as the starting compound.

8. A process according to claim 1, for the preparation of the compound of the formula

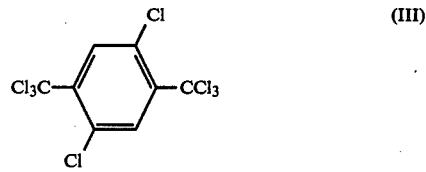

wherein 1,4-bis-(trichloromethyl)-benzene is reacted with chlorine to give the compound of the forumla (III).

* * * * *